United States Patent [19]

Atherton et al.

[11] 4,134,972
[45] Jan. 16, 1979

[54] COMPOSITIONS HAVING ANTIBIOTIC PROPERTIES

[75] Inventors: Frank R. Atherton, Welwyn Garden City; Michael J. Hall; Cedric H. Hassall, both of Welwyn; Peter S. Ringrose, Royston; Robert W. Lambert, Welwyn, all of England

[73] Assignee: Hoffmann-La Roche Inc., Nutley, N.J.

[21] Appl. No.: 850,742

[22] Filed: Nov. 11, 1977

Related U.S. Application Data

[60] Division of Ser. No. 707,158, Jul. 21, 1976, Pat. No. 4,100,275, which is a continuation-in-part of Ser. No. 650,336, Jan. 19, 1976, Pat. No. 4,016,148.

[51] Int. Cl.² ............... A61K 37/00; A61K 31/54; A61K 31/43
[52] U.S. Cl. ............... 424/177; 424/246; 424/271
[58] Field of Search ............... 424/177, 114, 271

[56] References Cited

U.S. PATENT DOCUMENTS

| | | | |
|---|---|---|---|
| 3,893,992 | 7/1975 | DeBenneville | 260/712.5 R |
| 3,923,877 | 12/1975 | Barton | 260/502.5 |
| 3,954,860 | 5/1976 | Birum | 260/502.5 |
| 3,969,398 | 7/1976 | Hershman | 260/502.5 |

*Primary Examiner*—Jerome D. Goldberg
*Attorney, Agent, or Firm*—Jon S. Saxe; Bernard S. Leon; George W. Johnston

[57] ABSTRACT

Compositions having antibiotic properties containing as antibiotic potentiators peptides of the formula

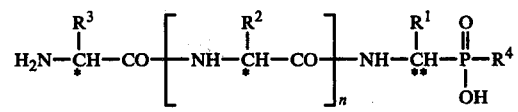

wherein $R^1$ represents a hydrogen atom or a lower alkyl, lower cycloalkyl, (lower cycloalkyl)-(lower alkyl), aryl or aryl(lower alkyl) group (said group being optionally substituted as the case may require by one or more amino, hydroxy, thio, methylthio, carboxy or guanidino groups so as to form the characterizing group of a naturally occurring L α-amino acid);

$R^2$ and $R^3$ each represent the characterizing group of an α-amino acid of the type normally found in proteins with the proviso that $R^3$ cannot represent a hydrogen atom when $n$ is zero and $R^1$ is a hydrogen atom or the phenyl group; $R^4$ represents a hydroxy or methyl group; $n$ stands for zero, 1, 2 or 3; and single asterisks denote that the configuration at the carbon atom so-marked is L when $R^2$ or $R^3$ as the case may be represents other than a hydrogen atom; and the double asterisk denotes that, when $R^1$ represents other than a hydrogen atom, the configuration at the carbon atom so-marked is (R) (as hereinafter defined), and an antibiotic are disclosed.

7 Claims, No Drawings

COMPOSITIONS HAVING ANTIBIOTIC PROPERTIES

RELATED APPLICATIONS

This is a division of application Ser. No. 707,158, filed July 21, 1976, now U.S. Pat. No. 4,100,275, which in turn is continuation-in-part of U.S. Patent Application Ser. No. 650,336, filed Jan. 19, 1976 now U.S. Pat. No. 4,016,148.

DETAILED DESCRIPTION OF THE INVENTION

The present invention is concerned with compositions having antibiotic properties and with a process for the manufacture of said compositions.

U.S. Patent Application Ser. No. 650,336 describes and claims peptides of the general formula

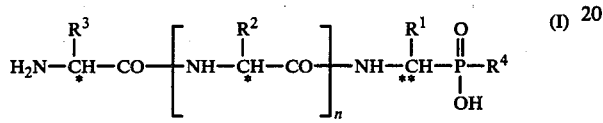

wherein $R^1$ represents a hydrogen atom or a lower alkyl, lower cycloalkyl, (lower cycloalkyl)-(lower alkyl), aryl or aryl-(lower alkyl) group (said groups being optionally substituted as the case may require by one or more amino, hydroxy, thio, methylthio, carboxy or guanidino groups so as to form the characterizing group of a naturally occurring L α-amino acid); $R^2$ and $R^3$ each represent the characterizing group of an α-amino acid of the type normally found in proteins with the proviso that $R^3$ cannot represent a hydrogen atom when n is zero and $R^1$ is a hydrogen atom or the phenyl group; $R^4$ represents a hydroxy or methyl group; n stands for zero, 1,2 or 3; and single asterisks denote that the configuration at the carbon atom so-marked is L when $R^2$ or $R^3$ as the case may be represents other than a hydrogen atom; and the double asterisk denotes that, when $R^1$ represents other than a hydrogen atom, the configuration at the carbon atom so-marked is (R) (as hereinafter defined), and their pharmaceutically acceptable salts. These peptides and their pharmaceutically acceptable salts potentiate the activity of antibiotics and also possess an antibacterial activity.

It has been found in accordance with the present invention that compositions comprising a peptide of formula I hereinbefore or a pharmaceutically acceptable acid addition salt thereof and an antibiotic selected from cephalothin, cephalexin, carbenicillin, ampicillin, penicillin G, sulbenicillin, cephazolin, cefoxitin, rifampicin, [(R)-1-(2-furoyloxy)-3-methylbutyl]penicillin, (6R)-6-[[(hexahydro-1H-azepin-1-yl)methylene]amino]-penicillanic acid, (pivaloyloxy)methtyl (6R)-6-[[(hexahydro-1H-azepin-1-yl)-methylene]amino]penicillanate, cephamandole, caphaloridin, cephaloglycin, phenethicillin, methicillin, propicillin, ticarcillin, amoxycillin arginine salt, phosphonomycin, vancomycin and kanamycin are of particular interest in view of the potentiation of the antibiotic which is achieved.

The present invention is based on the foregoing finding and is accordingly concerned with a composition having anti-biotic properties, said composition comprising a peptide of formula I hereinbefore or a pharmaceutically acceptable salt thereof and an antibiotic as hereinbefore set forth.

As used in this specification, the term "lower alkyl" means a straight-chain or branched-chain alkyl group which preferably contains from 1 to 6 carbon atoms (e.g. methyl, ethyl, propyl, isobutyl and the like). The term "lower cycloalkyl" comprises cyclic alkyl groups which contain from 3 to 6 carbon atoms. The term "aryl" preferably comprises mononuclear groups such as phenyl, which may be substituted in one or more positions with hydroxy, halogen, nitro, lower alkyl or lower alkoxy substituents. The term "halogen" means fluorine, chlorine, bromine and iodine and the term "lower alkoxy" means groups of the structure —O—(-lower alkyl) wherein the lower alkyl group is as defined earlier. The expression "the characterising group of an α-amino acid of the type normally found in proteins" is used to mean the residue R in a natural α-amino acid of the general formula

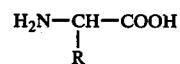

which is of the type normally occurring in proteins. Thus, for example, if the amino-acid is glycine then the residue R represents a hydrogen atom, in alanine the residue R represents the methyl group, in leucine the residue R represents the isobutyl group and in glutamic acid the residue R represents the 2-carboxyethyl group. R can also represent a residue which is linked with the amino nitrogen (with the loss of one of the hydrogen atoms attached thereto), thus forming a nitrogen-containing ring such as in proline and pyroglutamic acid.

When $R^1$ in formula I represents other than a hydrogen atom, the configuration at the carbon atom associated with a double asterisk is R; that is to say, the configuration which would be obtained by replacing the carboxyl group of a naturally occurring L α-amino acid by a phosphorus moiety.

It will be appreciated that when n in formula I stands for 2 or 3, the value of $R^2$ can be the same or different.

Preferred peptides of formula I hereinbefore are those in which $R^2$ and $R^3$ each represent a hydrogen atom or a methyl, isopropyl, isobutyl, benzyl, 4-aminobutyl or 2-pyrrolidinyl group, $R^1$ represents a hydrogen atom or a methyl group, $R^4$ represents a hydroxy group and n stands for zero or1.

Examples of peptides of formula I hereinbefore are:
(L-alanylamino)-methylphosphonic acid,
(L-valylamino)-methylphosphonic acid,
(L-leucylamino)-methylphosphonic acid,
(L-lysylamino)-methylphosphonic acid,
(L-phenylalanylamino)-methylphosphonic acid,
(1R)-1-(L-alanylamino)-ethylphosphonic acid,
(1R)-1-glycylamino-ethylphosphonic acid,
(1R)-1-(L-alanylamino)-benzylphosphonic acid,
(1R)-1-(L-prolylamino)-ethylphosphonic acid,
(1R)-1-(L-lysylamino)-ethylphosphonic acid,
(1R)-1-(L-leucylamino)-ethylphosphonic acid,
(1R)-1-(L-alanylamino)-2-phenyl-ethylphosphonic acid,
(1R)-1-(L-phenylalanylamino)-ethylphosphonic acid,
(1R)-1-(L-valylamino)-ethylphosphonic acid,
(L-alanyl-L-alanylamino)-methylphosphonic acid,
(L-leucyl-L-alanylamino)-methylphosphonic acid,
(L-alanyl-L-leucylamino)-methylphosphonic acid, (L-alanyl-L-phenylalanylamino)-methylphosphonic acid,
(L-phenylalanyl-L-phenylalanylamino)-methylphosphonic acid,
(L-phenylalanyl-L-alanylamino)-methylphosphonic acid,
(1R)-1-(L-alanyl-L-alanylamino)-ethylphosphonic acid,
(1R)-1-(glycyl-L-alanylamino)-ethylphosphonic acid,
(1R)-1-(L-valyl-L-alanylamino)-ethylphosphonic acid,
(1R)-1-(L-phenylalanyl-L-alanylamino)-ethylphosphonic acid,
(1R)-1-(L-prolyl-L-alanylamino)-ethylphosphonic acid,
(L-alanyl-L-alanyl-L-alanylamino)-methylphosphonic acid,
(1R)-1-(L-alanyl-L-alanyl-L-alanylamino)-ethylphosphonic acid,
(1R)-1-(glycyl-L-alanyl-L-alanylamino)-ethylphosphonic acid,
(1R)-1-(L-prolyl-L-alanyl-L-alanylamino)-ethylphosphonic acid,
(1R)-1-(glycyl-glycyl-L-alanylamino)-ethylphosphonic acid,
(1R)-1-(L-alanyl-L-alanyl-L-alanyl-L-alanylamino)-ethylphosphonic acid,
[(L-alanylamino)methyl]-methylphosphinic acid.

An especially preferred peptide of formula I is (1R)-1-(L-alanylamino)-ethylphosphonic acid.

The pharmaceutically acceptable salts of the peptides of formula I are salts formed with strong acids (e.g. methanesulphonic acid, paratoluenesulphonic acid, hydrochloric acid, hydrobromic acid, sulphuric acid etc) and with bases (e.g. sodium hydroxide etc).

The antibiotics referred to earlier are known substances and can be obtained according to methods known per se.

The weight ratio of the peptide of formula I or pharmaceutically acceptable salts thereof to antibiotic in the compositions provided by this invention can vary within wide limits. In general, the compositions can contain the peptide or pharmaceutically acceptable salt thereof and antibiotic in a ratio of from 1:100 to 100:1, preferably in a ratio of from 1:64 to 64:1 and especially in a ratio of from 1:16 to 16:1.

The process provided by the present invention for the manufacture of the compositions aforesaid comprises mixing a peptide of formula I or a pharmaceutically acceptable salt thereof with an antibiotic aforesaid.

The process provided by the present invention can be carried out in a manner known per se. In a preferred aspect of the process, the peptide of formula I or pharmaceutically acceptable salt thereof and antibiotic are used in a weight ratio of from 1:100 to 100:1, especially in a weight ratio of 1:64 to 64:1 and more especially in a weight ratio of 1:16 to 16:1.

The compositions provided by the present invention are active against a wide range of gram-positive and gram-negative bacteria such as, for example, Escherichia coli, Proteus mirabilis, Proteus vulgaris, Pseudomonas aeruginosa Staphylococcus aureus, Streptococcus faecalis, Klebsiella aerogenes and Klebsiella pneumoniae. They are accordingly suitable for combating and preventing a wide range of bacterial infections. The compositions provided by the present invention may be administered orally or parenterally, the oral route of administration being preferred.

The in vitro activity of the compositions provided by the present invention can be demonstrated as follows:

Mixtures of the peptide of formula I and antibiotic were prepared in concentrated solutions at the desired ratios. Dilutions were then effected to give an acceptable range of total concentrations of the mixtures. Aliquots of the dilutions were mixed with an appropriate nutrient agar in petri dishes and the agar was allowed to set. Similar sets of dishes were prepared using nutrient agar containing the peptide alone and the antibiotic alone. Test organisms were then inoculated on to the surface on the agar using a multipoint inoculation device. The dishes were then stored at 37° C for 24 hours, after which time the minimum inhibitory concentrations (M.I.C.) were read and the fractional inhibitory concentration indices (F.I.C.) were calculated. The results obtained using a representative peptide of formula I, namely (1R)-1-(L-alanylamino)-ethylphosphonic acid, and representative antibiotics aforesaid are given in Tables I and II hereinafter:

Table I

Activity of combinations of various antibiotics with the peptide (1R)-1-(L-alanylamino)-ethylphosphonic acid against *Staphylococcus aureus*

| Antibiotic | M.I.C. (µg/ml) Antibiotic alone | M.I.C. (µg/ml) Combination | Ratio of antibiotic to peptide | F.I.C. Index |
|---|---|---|---|---|
| Cephalexin | 4.0 | 0.012 + 0.00038 | 32:1 | 0.003 |
| Cephalexin | 4.0 | 0.125 + 0.125 | 1:1 | 0.045 |
| Cephalexin | 4.0 | 0.03 + 0.97 | 1:32 | 0.13 |
| Cephazolin | 0.5 | 0.12 + 1.88 | 1:16 | 0.3 |
| Cephamandole | 0.5 | 0.05 + 0.2 | 1:4 | 0.15 |
| Cephoxitin | 0.5 | 0.084 + 0.042 | 2:1 | 0.25 |
| Sulbenicillin | 0.5 | 0.05 + 0.2 | 1:4 | 0.15 |
| Methicillin | 1.0 | 0.056 + 0.44 | 1:8 | 0.11 |
| Amoxycillin arginine salt | 4.0 | 1.0 + 0.25 | 4:1 | 0.31 |
| (6R)-6-[[(Hexahydro-1H-azepin-1-yl)methyleneamino]penicillanic acid | 8.0 | 0.12 + 3.88 | 1:32 | 0.26 |
| Rifampicin | 0.39 | 0.024 + 6.25 | 1:260 | 0.11 |

Table II

Activity of combinations of various antibiotics with the peptide (1R)-1-(L-alanylamino)-ethylphosphonic acid against strains of *Klebsiella aerogenes* and *Proteus Mirabilis*

| Antibiotic | Organism | M.I.C. (µg/ml) Antibiotic alone | M.I.C. (µg/ml) Combination | Ratio of antibiotic to peptide | F.I.C. Index |
|---|---|---|---|---|---|
| Cephalexin | K. aerogenes | 2.0 | 0.05 + 0.2 | 1:4 | 0.225 |
| Cephalexin | P. mirabilis | 128.0 | 14.2 + 1.8 | 8:1 | 0.12 |
| Cephoxitin | K. aerogenes | 4.0 | 0.33 + 0.66 | 1:2 | 0.16 |
| Cephamandole | K. aerogenes | 128.0 | 1.6 + 6.4 | 1:4 | 0.06 |
| Cephamandole | P. mirabilis | 2.0 | 0.66 + 0.33 | 2:1 | 0.33 |
| Methicillin | K. aerogenes | 256.0 | 0.89 + 0.11 | 8:1 | 0.44 |
| Sulbenicillin | K. aerogenes | 8.0 | 0.25 + 0.25 | 1:1 | 0.06 |

Table II-continued

Activity of combinations of various antibiotics with the peptide (1R)-1-(L-alanylamino)-ethylphosphonic acid against strains of *Klebsiella aerogenes* and *Proteus Mirabilis*

| Antibiotic | Organism | M.I.C. (μg/ml) Antibiotic alone | M.I.C. (μg/ml) Combination | Ratio of antibiotic to peptide | F.I.C. Index |
|---|---|---|---|---|---|
| (6R)-6-[[(hexa-hydro-1H-azepin-1--yl)methyl-ene]amino]-penicillanic acid | *P. mirabilis* | 128.0 | 16.0 + 16.0 | 1:1 | 0.25 |

The in vivo activity of the compositions provided by the present invention can be demonstrated as follows:

Mice are infected intraperitoneally with 5-10 times the $LD_9$ of the infecting organism. At predetermined time intervals after the infection, groups of mice are dosed subcutaneously with graded doses of the antibiotic, peptide and all combinations thereof. The number of mice surviving on each treatment for 7 days after infection is noted and the dose preventing death in 50% of the mice ($CD_{50}$) is calculated. The fractional inhibitory concentration (F.I.C.) index for a combination of antibiotic and peptide is calculated in the normal manner. The results obtained using (1R)-1-(L-alanylamino)-ethylphosphonic acid as an example of a peptide of formula I and representative antibiotics aforesaid are given in Table III hereinafter:

Table III

Chemotherapeutic activity ($CD_{50}$ mg/kg subcutaneous) of combinations of various antibiotics with the peptide (1R)-1-(L-alanylamino)-ethylphosphonic acid against bacterial infections in the mouse

| Antibiotic | Infecting organism | $CD_{50}$ antibiotic | $CD_{50}$ peptide | $CD_{50}$ combination | Ratio of peptide to antibiotic | F.I.C. Index |
|---|---|---|---|---|---|---|
| Carbenicillin | *S. aureus* PS | 17.75 | >1000 | 29.5 | 10:1 | ≦0.15 |
| Penicillin G | *E. coli* | 8.03 | 43.7 | 5.8 | 1:1 | 0.36 |
| [(R)-1-(2-Furo-yloxy-3-methyl-butyl]penicillin | *E. coli* | 15.7 | 43.7 | 8.2 | 1:1 | 0.25 |
| Ampicillin | *K. aerogenes* | >400 | 283 | 123 | 1:1 | ≦0.37 |
| (6R)-6-[[(hexa-hydro-1H-azepin--1-yl)methyl-enelamino]-penicillanic acid | *E. coli* | 0.86 | 4.19 | 1.15 | 5:1 | 0.22 |
| Cephalexin | *S. aureus* PS | 1.7 | >1000 | 6.6 | 10:1 | ≦0.35 |
| Cephalexin | *S. aureus* PR | 44.1 | > 400 | 18.5 | 1:1 | ≦0.2 |
| Cephalexin | *K. pneumoniae* | >125 | > 125 | 44.2 | 1:1 | ≦0.2 |
| Cephalexin | *Strep. pyogenes* | 2.0 | >1000 | 9.8 | 10:1 | ≦0.46 |
| Cephalothin | *S. aureus* | 3.5 | >1000 | 11.1 | 10:1 | ≦0.3 |
| Manamycin | *S. aureus* | 223 | >1000 | 107 | 1:1 | ≦0.3 |

The compositions provided by the present invention can be administered in the form of pharmaceutical preparations. Such preparations also form part of the present invention and comprise a peptide of formula I hereinbefore or a pharmaceutically acceptable salt thereof, an antibiotic as hereinbefore set forth and a pharmaceutically acceptable carrier material.

The pharmaceutically acceptable carrier material present in the pharmaceutical preparations provided by this invention can be any solid or liquid carrier material which is compatible with the peptides of formula I and their pharmaceutically acceptable salts and with the antibiotics specified earlier and which is suitable for therapeutic administration. The carrier material can be an organic or inorganic carrier material which is suitable for enteral (e.g. oral) or parenteral administration. Examples of such carrier materials are water, gelatin, lactose, starches, magnesium stearate, talc,, vegetable oils, gum arabic, polyalkyleneglycols, petroleum jelly and the like.

The pharmaceutical preparations can be prepared in a manner known per se.

The pharmaceutical preparations can be made up in a solid form (e.g. as tablets, dragées, suppositories or capsules) or in a liquid form (e.g. as solutions, suspensions or emulsions). The pharmaceutical preparations may be subjected to conventional pharmaceutical operations such as sterilisation and may contain adjuvants such as preserving agents, stabilising agents, wetting agents, emulsifying agents, salts for varying the osmotic pressure or buffers. When a buffer is used, the pH of the preparation will, of course, vary within a range which is well-known in pharmaceutical practice.

The amount of peptide of formula I of pharmaceutically acceptable salt thereof and antibiotic present in the pharmaceutical preparations provided by this invention will vary within wide limits depending on factors such as the particular peptide or salt thereof chosen, the particular antibiotic chosen, the route of administration and the infection to be treated. The dosage administered daily will also vary within wide limits and will be suited to individual requirement and fitted to the exigencies of a particular situation as determined by the prescribing physician. For example, a daily dosage for oral administration may amount to 750 mg to 1500 mg of a combination of the active ingredients (i.e., a peptide of formula I or pharmaceutically acceptable salt thereof and antibiotic). Again, for example, a daily dosage for parenteral administration may amount to about 200 mg to 2000 mg of a combination of active ingredients. Daily dosages can be administered in a single dosage or in divided dosages.

The peptides of formula I hereinbefore and their pharmaceutically acceptable salts can be prepared by (a) cleaving off by methods known per se the protecting group(s) present in a compound of the general formula

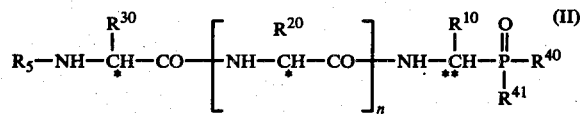

, wherein the symbols $R^{10}$, $R^{20}$ and $R^{30}$ have any of the values accorded to the symbols $R^1$, $R^2$ and $R^3$ hereinbefore respectively except that any amino group or amino groups present may be in protected form and any other functional group which may be present is in protected form where required, $R^{40}$ represents a methyl group or $R^{41}$, $R^{41}$ represents a hydroxy group or lower alkoxy protecting group, $R^5$ represents a hydrogen atom or a protecting group, and the single and double asterisks as well as n have the significances given earlier, or (b) separating an (R,S)-diastereomeric peptide corresponding to formula I into its diastereomers and isolating the (R)-diastereomer, and, if desired, converting an obtained peptide of formula I into a pharmaceutically acceptable salt.

The amino group or amino groups which may be present in $R^{10}$, $R^{20}$ and $R^{30}$ in formula II can be protected with any amino-protecting group which is well-known in peptide chemistry. Especially suitable amino-protecting groups for the purpose of the present invention are aralkoxycarbonyl groups, particularly the benzyloxycarbonyl group, and the tertbutoxycarbonyl group. The amino-protecting group may also be a formyl, trityl or trifluoroacetyl group. Any carboxy or hydroxy group which may be present in $R^{10}$, $R^{20}$ and $R^{30}$ in formula II can be protected by a conventional carboxy-protecting or hydroxy-protecting group respectively. For example, a carboxy group may be protected by conversion into an alkyl ester (e.g. a tertbutyl ester) or an aralkyl ester (e.g. a benzyl ester). Again, for example, a hydroxy group may be protected, for example, by means of an aralkoxycarbonyl group (e.g. benzyloxcarbonyl), an alkanoyl group (e.g. acetyl, propionyl etc), an aroyl group (e.g. benzoyl), an alkyl group (e.g. tertbutyl) or an aralkyl group (e.g. benzyl). The protection of other functional groups present in $R^{10}$, $R^{20}$ and $R^{30}$ may be carried out in a known manner. The protecting group denoted by $R^5$ in formula II can be any of the amino-protecting groups mentioned earlier in connection with $T^{10}$, $R^{20}$ and $R^{30}$.

The cleavage of the protecting group or protecting groups present in a compound of formula II is carried out in accordance with methods known per se; that is to say, methods in actual use for or described in the literature on the cleavage of protecting groups. Thus, for example, an aralkoxycarbonyl group (e.g. benzyloxycarbonyl) or a tertbutoxycarbonyl group may be cleaved off by hydrolysis (e.g. treatment with a mixture of hydrogen bromide and glacial acetic acid). An aralkoxycarbonyl group (e.g. benzyloxycarbonyl) can also be cleaved off by hydrogenolysis (e.g. in the presence of palladium-on-charcoal). The tertbutoxycarbonyl group may also be cleaved off by means of hydrogen chloride in dioxan. A lower alkoxy group denoted by $R^{40}$ and/or $R^{41}$ may be converted into a hydroxy group by treatment with a mixture of hydrogen bromide in glacial acetic acid or by means of trimethylchlorosilane followed by aqueous hydrolysis. It will be appreciated that the cleavage of the protecting groups can be carried out in a single step or in more than one step depending on the nature of the protecting groups present.

The separation of an (R,S)-diastereomeric peptide corresponding to formula I into its diastereomers and isolation of the (R)-diastereomer can be carried out according to known methods; for example, by fractional crystallisation or by high pressure liquid chromatography.

The compounds of formula II hereinbefore may be prepared, for example, by condensing a compound of the general formula

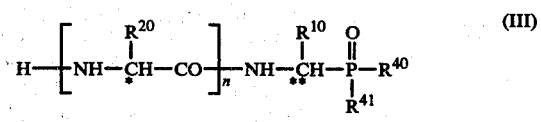

, wherein $R^{10}$, $R^{20}$, $R^{40}$, $R^{41}$, n and the single and double asterisk have the significance given earlier, with an appropriately protected α-amino acid, an appropriately protected dipeptide, an appropriately protected tripeptide, an appropriately protected tetrapeptide or a reactive derivative thereof as the case may require.

Thus, when a compound formula III in which n stands for zero is used, such a compound can be condensed with an appropriately protected α-amino acid or a reactive derivative thereof to give a compound of formula II in which n stands for zero, or with an appropriately protected dipeptide or a reactive derivative thereof to give a compound of formula II in which n stands for 1, or with an appropriately protected tripeptide or a reactive derivative thereof to give a compound of formula II in which $n$ stands for 2 or with an appropriately protected tetrapeptide or a reactive derivative thereof to give a compound of formula II in which $n$ stands for 3.

Again, a compound of formula III in which n stands for 1 can be condensed with an appropriately protected α-amino acid or a reactive derivative thereof to give a compound of formula II in which $n$ stands for 1, or with an appropriately protected dipeptide or a reactive derivative thereof to give a compound of formula II in which $n$ stands for 2 or with an appropriately protected tripeptide or a reactive derivative thereof to give a compound of formula II in which n stands for 3.

Yet again, a compound of formula III in which n stands for 2 can be condensed with an appropriately protected α-amino acid or a reactive derivative thereof to give a compound of formula II in which $n$ stands for 2 or with an appropriately protected dipeptide or a reactive derivative thereof to give a compound of formula II in which $n$ stands for 3.

Finally, a compound of formula III in which $n$ stands for 3 can be condensed with an appropriately protected α-amino acid or a reactive derivative thereof to give a compound of formula II in which n stands for 3.

Alternatively, the compounds of formula II can be prepared by carrying out the foregoing condensation using an (R,S) compound corresponding to formula III and separating the (R) compound from the resulting (R,S) product in a manner known per se; for example, by crystallisation, chromatography or fractional crystallisation using a suitable base such as α-methylbenzylamine.

The aforementioned condensation can be carried out in accordance with methods which are known per se in peptide chemistry; for example, by the mixed anhydride, azide, activated ester or acid chloride method.

In one method, an appropriate compound of formula III can be condensed with an appropriately protected amino acid, di-, tri- or tetrapeptide as the case may require in which the terminal carboxy function is a mixed anhydride residue formed with an organic or inorganic acid. Suitably, such an amino acid, di-, tri- or tetrapeptide carrying a free carboxy function is treated with a tertiary base such as a tri(lower alkyl)amine (e.g. triethylamine) or N-ethylmorpholine in an inert organic solvent (e.g. tetrahydrofuran, 1,2-dimethoxyethane, dichloromethane, toluene, petroleum ether or mixtures thereof) and the resulting salt is reacted with a chloroformic acid ester (e.g. the ethyl or isobutyl ester) at a low temperature. The mixed anhydride obtained is then suitably condensed in situ with the compound of formula III.

In another method, an appropriate compound of formula III can be condensed with an appropriately protected amino acid, di-, tri- or tetrapeptide as the case may require in which the terminal carboxy group is in the form of an acid azide. This condensation is preferably carried out in an inert organic solvent such as dimethylformamide or ethyl acetate at a low temperature.

In yet another method, an appropriate compound of formula III can be condensed with an appropriately protected amino acid, di-, tri- pr tetrapeptide as the case may require in which the terminal carboxy function is in the form of an active ester group (e.g. the p-nitrophenyl, 2,4,5-trichlorophenyl or N-hydroxysuccinimide ester group). This condensation is suitably carried out either in an inert organic solvent such as dimethylformamide or, in the case where $R^{40}$ and/or $R^{41}$ represents a lower alkoxy group, in an aqueous alkanol (e.g. aqueous ethanol).

In a further method, an appropriate compound of formula III can be condensed with an appropriately protected amino acid, di-, tri- or tetrapeptide as the case may require in which the terminal carboxy function is in the form of an acid chloride. This condensation is preferably carried out in the presence of a base and at a low temperature.

The following Examples illustrate the pharmaceutical preparations provided by the present invention:

EXAMPLE 1

Hard gelatin capsules containing the following ingredients are prepared:

| Ingredient | Per capsule |
| --- | --- |
| (1R)-1-(L-Alanylamino)-ethylphosphonic acid | 250.0 mg |
| Cephalexin | 25.0 mg |
| Corn starch | 20.0 mg |
| Aerosol OT | 0.5 mg |
| Aerosil | 2.5 mg |
| Total weight | 298.0 mg |

The (1R)-1-(L-alanylamino)-ethylphosphonic acid and cephalexin are individually milled, mixed together and the mixture is granulated with a 10% corn starch paste containing Aerosol OT. The wet granulate is dried, passed through a sieve, mixed with the Aerosil and finally filled into hard gelatin capsules.

EXAMPLE 2

Hard gelatin capsules containing the following ingredients are prepared:

| Ingredient | Per capsule |
| --- | --- |
| (1R)-1-(L-Alanylamino)-ethylphosphonic acid | 125.0 mg |
| Cephalexin | 125.0 mg |
| Corn starch | 20.0 mg |
| Aerosol OT | 0.5 mg |
| Aerosil | 2.5 mg |
| Total weight | 273.0 mg |

The preparation of these capsules is carried out in a manner analogous to that described in Example 1.

EXAMPLE 3

A powder mixture for preparing an injection solution contains the following ingredients:

| | |
| --- | --- |
| (6R)-6-[[(Hexahydro-1H-azepin-1-yl)methylene]amino]penicillanic acid | 200.0 mg |
| (1R)-1-(L-Alanylamino)-ethylphosphonic acid | 200.0 mg |
| Sodium citrate | 20.0 mg |

The foregoing ingredients are individually milled and then thoroughly mixed together. The mixture is filled into suitable containers under sterile conditions and the containers are sealed.

In order to prepare an injection solution, the foregoing powder mixture is dissolved in 2 ml of water for injection.

EXAMPLE 4

An injection solution is prepared by dissolving 1.0 g of penicillin G in 2 ml of a solution containing 100 mg of (1R)-1-(L-alanylamino)-ethylphosphonic acid per ml of a suitable buffer. A suitable buffer contains the following ingredients:

| | |
| --- | --- |
| Sodium chloride | 8.3 mg |
| Chlorocresol | 1.0 mg |
| Glacial acetic acid | 1.2 mg |
| sodium hydroxide q.s. ad | pH 4.5 |
| Water for injection ad | ml |

The following Examples illustrate in detail the manner in which the aforementioned (1R)-1-(L-alanylamino)-ethylphosphonic acid can be prepared:

EXAMPLE A 14.1 g (0.168 mol) of solid sodium bicarbonate were added to a solution of 7 g (0.056 mol) of (1R,S)-1-aminoethylphosphonic acid in 280 ml of water and 140 ml of ethanol while stirring at 0° C. While stirring this mixture at 0° C, a solution of 17.9 g (0.056 mol) of the N-hydroxysuccinimide ester of N-benzyloxycarbonyl-L-alanine in 140 ml of warm ethanol was added dropwise over ca 15 minutes. The latter solution was washed in with 70 ml of ethanol. The heterogeneous mixture was stirred for 1 hour at 0° C and then for a further 16 hours at room temperature, the mixture becoming homogeneous. The mixture was evaporated and re-evaporated with 200 ml of water to give a gum which was dissolved in 500 ml of water. The solution was extracted firstly with 500 ml of chloroform and then with two 250 ml portions of chloroform, acidified to pH 2 with ca 80 ml of 2-N hydrochloric acid and again extracted with 500 ml of chloroform followed by two 250 ml portions of chloroform. The aqueous layer was concentrated and passed down a column of cation exchange resin (B.D.H., Zerolit 225, SRC 13, RSO$_3$H; 750 g; freshly regenerated in the acid cycle). The column was eluted with water and there were collected six 250 ml fractions. The first four fractions were combined, evaporated and re-evaporated with water to remove hydrogen chloride. There was obtained a final residue of (1R,S)-1-[(N-benzyloxycarbonyl-L-alanyl)-amino]-ethylphosphonic acid which was separated as follows:

The latter residue was dissolved in 400 ml of water and titrated with 1-M benzylamine to pH 4.5; titre 75 ml; theory 56 ml. The resulting solution was concentrated and crystallised from water to give 5.3 g of the benzylamine salt of (1 S)-1-[(N-benzyloxycarbonyl-L-alanyl)amino]-ethylphosphonic acid of melting point 210°–215° C. Concentration of the mother liquors followed by further recrystallisation from water gave the benzylamine salt of (1R)-1-[(N-benzyloxycarbonyl-L-alanyl(amino]-ethylphosphonic acid in a first crop of 0.59 g [melting point 226°–228° C (decomposition); $[\alpha]_D^{20} = -32.3°$ (c = 1% in acetic acid)] and a second crop of 0.825 g [melting point 225°–227° C (decomposition); $[\alpha]_D^{20} = -33.0°$ (c = 1% in acetic acid)]. Recrystallisation of the first crop from water gave 0.333 g of pure benzylamine salt of the R-stereoisomer; melting point 226°–228° C (decomposition); $[\alpha]_D^{20} = -33.1°$ (c = 1% in acetic acid).

1.1 g (2.5 mmol) of the benzylamine salt of (1R)-1-[(N-benzyloxycarbonyl-L-alanyl)amino]-ethylphosphonic acid were dissolved in 4 ml of 2-N ammonium hydroxide, passed down a column of cation exchange resin B.D.H., Zerolit 225, SRC 13, RSO$_3$H; 120 g; freshly regenerated in the acid cycle) and eluted with water. There were collected 220 ml of acid eluate which was concentrated to 100 ml. To this were added successively 100 ml of methanol, 0.3 g of 5% palladium-on-charcoal catalyst and 3 drops of glacial acetic acid. The mixture was hydrogenated at room temperature and atmospheric pressure. The catalyst was filtered off and the solvent evaporated. The residual gum was re-evaporated with three 50 ml portions of n-propanol to give 0.6 g of a gummy solid of melting point ca 275°–280° C (decomposition). After further recrystallisation from water and ethanol, there was obtained 0.2 g of (1R)-1-(L-alanylamino)-ethylphosphonic acid of melting point 295°–296° C (decomposition); $[\alpha]_D^{20} = -44.0°$ (c = 1% in water).

EXAMPLE B

A solution of 30 g (0.24 mol) of (1R,S)-1-aminoethylphosphonic acid in 120 ml (0.48 mol) of 4-N sodium hydroxide was stirred at 14° C while 180 ml (0.72 mol) of a solution of 4-N sodium hydroxide and 102 g (0.60 mol) of benzyl chloroformate were added alternately in four portions. The stirring was continued and after a further 2 hours the temperature had risen to 20° C. The mixture was stirred for a further 16 hours at room temperature. 600 ml of ether were then added and the mixture was stirred vigorously for 2 hours to extract the excess benzyl chloroformate. The layers were separated and the aqueous layer was acidified to pH 2 with ca 110 ml of 5-N hydrochloric acid while maintaining the temperature below 10° C. The resulting slurry was concentrated to a low bulk to remove carbon dioxide. The residue was dissolved in 100 ml of 2-N sodium hydroxide and 50 ml of water, passed down a column of cation exchange resin (B.D.H., Zerolit 225, SRC 13, RSO$_3$H; 750 g; freshly regenerated in the acid cycle) and eluted with water. There were obtained ca 3.2 liters of acid eluate which were evaporated at room temperature and re-evaporated with three 500 ml portions of water. The residue was dissolved in water and allowed to crystallise. The crystals were filtered off, washed with ice-cold water and dried; yield 39.2 g; melting point 111°–113° C (decomposition). Evaporation of the combined filtrates followed by crystallisation from 75 ml of water and 10 ml of methanol and refrigeration, gave a further yield of 6.51 g; melting point 110°–112° C (decomposition). There was obtained a total of 45.71 g of (1R,S)-1-(benzyloxycarbonylamino)-ethylphosphonic acid, which was characterised as the monobenzylamine salt of melting point 196°–197° C (decomposition).

42.2 g (163 mmol) of (1R,S)-1-(benzyloxycarbonyl-amino)-ethylphosphonic acid were dissolved in 100 ml of methanol. The solution was treated with a solution of 30.8 g (81.5 mmol) of quinine trihydrate in 100 ml of methanol and the mixture was stored for 3 hours at room temperature and then overnight at 0° C. The quinine salt of (1S)-1-(benzyloxycarbonyl-amino)-ethylphosphonic acid was filtered off and washed with methanol. The combined filtrates were evaporated and the resiude was dissolved in 300 ml of 2-N ammonium hydroxide. The solution was extracted with three 300 ml portions of chloroform. Each chloroform extract was back-washed with 150 ml of water. The aqueous extracts were combined, concentrated and then passed down a column of cation exchange resin (B.D.H., Zerolit 225, SCR 13 RSO$_3$H; 750 g; freshly regenerated in the acid cycle). Elution with water gave ca 2.3 liters of acid eluate, which was evaporated. The residue was re-evaporated firstly with three 200 ml portions of water and then with three 300 ml portions of methanol to give ca 24 g of a residual gum. This gum was dissolved in 100 ml of dry methanol and treated with a solution of dehydroabietylamine [82 mmol; freshly regenerated from 28.4 g (82 mmol) of dehydroabietylamine acetate with ammonium hydroxide/petroleum ether]. The mixture was stood at 0° C, filtered and the filtrate was washed with methanol and ether. There were obtained 47.4 g of crude dehydroabietylamine salt of (1R)-1-(benzyloxycarbonyl-amino)-ethylphosphonic acid of melting point 189°–194° C (decomposition); $[\alpha]_D^{20} = +16.8°$ (c = 0.5% in methanol). Further recrystallisation from methanol and water gave 33.0 g of the pure dehydroabietylamine salt of (1R)-1-(benzyloxycarbonly-amino)-ethylphosphonic acid of melting point 202°–205° C (decomposition); $[\alpha]_D^{20} = +18.1°$ (c = 0.5% in methanol).

8.0 g (14 mmol) of the dehydroabietylamine salt of (1R)-1-(benzyloxycarbonyl-amino)-ethylphosphonic acid were partitioned between 100 ml of 2-N ammonium hydroxide and 100 ml of petroleum ether (boiling point range 60°–80° C). The mixture was shaken vigorously and then the layers were separated. The aqueous layer was extracted with two 50 ml portions of petroleum ether. Each petroleum ether extract was then back-extracted with two 50 ml portions of water. The aqueous extracts were combined and evaporated at room temperature to give an oil. This oil was dissolved in water, passed down a column of cation exchange resin (B.D.H., Zerolit 225, SRC 13, RSO₃H; 250 g; freshly regenerated in the acid cycle) and eluted with water. There were obtained 800 ml of an acid fraction which was then concentrated to 400 ml. To this concentrate were added successively 2.0 g of 10% palladium-on-charcoal catalyst, 400 ml of methanol and 0.2 ml of glacial acetic acid. The mixture was then hydrogenated. The catalyst was filtered off and the solvent evaporated. The residue was re-evaporated with three 100 ml portions of n-propanol and triturated with ether to give a solid of melting point ca 285°–288° C (decomposition). Recrystallisation from water and ethanol gave 1.0 g of (1R)-1-aminoethylphosphonic acid of melting point 294°–295° C (decomposition); $[\alpha]_D^{20} = -16.9°$ (c = 2% in 1-N sodium hydroxide).

0.4 g (3.2 mmol) of (1R)-1-aminoethylphosphonic acid in 14 ml of water and 7 ml of ethanol were stirred at 10° C while 0.806 g (9.6 mmol) of sodium bicarbonate were added portionwise. The mixture was then stirred at 0° C while a hot solution of 1.024 g (3.2 mmol) of the N-hydroxysuccinimide ester of N-benzyloxycarbonyl-L-alanine in 8 ml of ethanol was added rapidly dropwise. The mixture was stirred for 3 hours at 0° C and then for 16 hours at room temperature. The mixture was worked up in a manner analogous to that described in the penultimate paragraph of Example A by passage down a column of cation exchange resin and conversion to the benzylamine salt. There were obtained 0.26 g of the benzylamine salt of (LR)-1-[(N-benzyloxycarbonyl-L-alanyl)amino]-ethylphosphonic acid of melting point 229°–231° C (decomposition); $[\alpha]_D^{20} = -34.2°$ (c = 1% in glacial acetic acid).

In a manner analogous to that described in the last paragraph of Example A, starting from the benzylamine salt of (1R)-1-[(N-benzyloxycarbonyl-L-alanyl)amino]-ethylphosphonic acid there was obtained (1R)-1-(L-alanylamino)-ethylphosphonic acid of melting point 295°–296° C (decomposition); $[\alpha]_D^{20} = -45.6°$ (c = 1% in water).

EXAMPLE C 139.7 g (0.5 mol) of dimethyl 1-benzylaminoethyl phosphonate hydrochloride were dissolved in 1000 ml of methanol. The solution was hydrogenated at room temperature and atmospheric pressure in the presence of 15 g of 10% palladium-on-charcoal for several hours until the hydrogen uptake ceased. The catalyst was filtered off and the filtrate evaporated in vacuo. The residue of dimethyl 1-aminoethylphosphonate hydrochloride was dissolved in 500 ml of dry dimethylformamide and then treated with 160 g (0.5 mol) of the N-hydroxysuccinimide ester of N-benzyloxycarbonyl L-alanine. While stirring and maintaining the temperature below 0° C, there were added dropwise 70 ml of dry triethylamine. The mixture was then stirred overnight at room temperature. The triethylamine hydrochloride was filtered off and washed with a small amount of dimethylformamide. The filtrate was evaporated under an oil-pump vacuum and at a temperature below 40° C. The residual oil was treated with water and the resulting mixture extracted with portions of chloroform. The combined organic phases were washed with a small volume of a strong potassium carbonate solution and then dried over sodium sulphate. The sodium sulphate was filtered off and the filtrate evaporated, first under a water-pump vacuum and then under an oil-pump vacuum. There was obtained a residue which, on treatment with 600 ml of dry ether, gave 72.5 g of dimethyl (1S)-1-[(N-benzyloxycarbonyl-L-alanyl)amino]-ethylphosphonate of melting point 134°–135° C; $[\alpha]_D^{20} = +14.9°$ (c = 1% in methanol). Evaporation of the mother liquors gave ca 100 g of a gum consisting substantially of the corresponding R-isomer.

100 g of the gum obtained according to the first paragraph described in this Example were treated with 250 ml of a 45% solution of hydrogen bromide in glacial acetic acid for 5 hours at room temperature. 750 ml of ether were then added while stirring, the stirring was discontinued and the ether decanted. This procedure was repeated with two further 250 ml portions of ether. The residue was dissolved in 250 ml of methanol and to the resulting solution was added a solution of 50 ml of propylene oxide in 50 ml of methanol. After standing for several hours, the resulting precipitate was filtered off and washed with methanol and ether. The product was dried to a constant weight of 46.1 g and then had a melting point of 283°–285° C (decomposition). Recrystallisation from water/ethanol mixtures yielded 36.5 g of (1R)-1-(L-alanylamino)-ethylphosphonic acid of melting point 295°–296° C (decomposition); $[\alpha]_D^{20} = -46.3°$ (c = 1% in water).

What we claim is:

1. An antibacterial pharmaceutical composition containing
   (1) a peptide represented by the formula

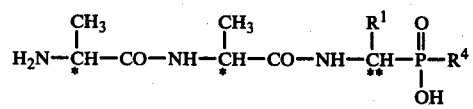

wherein R¹ is hydrogen, lower alkyl, lower cycloalkyl, (lower cycloalkyl)-(lower alkyl), aryl, aryl-(lower alkyl), said R¹ substituents being substituted, if required, by one or more amino, hydroxy, thio, methyl thio, carboxy, or guanidino to form the characterizing group of a naturally occurring L α-amino acid; R⁴ is hydroxy or methyl; the single asterisk denotes the L configuration at the carbon so marked; the double asterisk denotes the R configuration at the carbon so marked when R¹ is other than hydrogen, or a pharmaceutically acceptable salt thereof; and
   (2) an antibiotic selected from the group consisting of carbenicillin, ampicillin, penicillin G, sulbenicillin, [(R)-1-(2-furoyloxy)-3-methylbutyl]-penicillin,(6R)-6-[[(hexahydro-1H-azepin-1-yl)methylene]-amino]penicillanic acid,(pivaloyloxy)-methyl (6R)-6-[[(hexahydro-1H-azepin-1-yl)methylene]amino]penicillanate, phenethicillin, methicillin, propicillin, ticarcillin and amoxycillin arginine salt;

wherein the weight ratio of the peptide or pharmaceutically acceptable salt thereof to said antibiotic is from 1:100 to 100:1.

2. The composition of claim 1 wherein said peptide is (1R)-1-(L-alanyl-L-alanylamino)-ethylphosphonic acid.

3. The composition of claim 1 wherein said antibiotic is ampicillin.

4. The composition of claim 1 wherein the weight ratio of said peptide or pharmaceutically acceptable salt thereof to said antibiotic is from 1:64 to 64:1.

5. The composition of claim 1 wherein the weight ratio of said peptide or pharmaceutically acceptable salt thereof to said antibiotic is from 1:16 to 16:1.

6. The composition of claim 1 wherein the antibiotic is (6R)-6-[[(hexahydro-1H-azepin-1-yl)methylene]amino]penicillanic acid.

7. The composition of claim 1 wherein the antibiotic is (pivaloyloxy)methyl (6R)-6-[[(hexahydro-1H-azepin-1-yl)methylene]amino]-amino]

* * * * *